US006955920B1

(12) United States Patent
Baugh et al.

(10) Patent No.: US 6,955,920 B1
(45) Date of Patent: Oct. 18, 2005

(54) TEST CARTRIDGE FOR EVALUATING BLOOD PLATELET FUNCTIONALITY

(75) Inventors: Robert F. Baugh, Parker, CO (US); Carole G. Lane, Greenwood Village, CO (US); Adrian C. Wilson, Denver, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/330,544

(22) Filed: Jun. 11, 1999

Related U.S. Application Data

(62) Division of application No. 08/640,275, filed on Apr. 30, 1996, now Pat. No. 5,925,319.

(51) Int. Cl.[7] .............................................. G01N 33/86
(52) U.S. Cl. ........................... 436/69; 422/73; 73/54.01
(58) Field of Search .............................. 436/69, 55, 10; 422/73; 73/54.01, 54.13, 54.14, 54.17, 54.11

(56) References Cited

U.S. PATENT DOCUMENTS

| | | | |
|---|---|---|---|
| 3,077,106 A | 2/1963 | Fink ................................ 73/53 |
| 3,307,392 A | 3/1967 | Owen et al. ................... 73/64.1 |
| 3,450,501 A | 6/1969 | Oberhardt ..................... 23/253 |
| 3,492,096 A | 1/1970 | Hattersley .................... 23/230 |
| 3,560,162 A | 2/1971 | Mittleman .................... 23/253 |
| 3,560,163 A | 2/1971 | Mittleman .................... 23/253 |
| 3,587,295 A | 6/1971 | Simons ........................ 73/64.1 |
| 3,635,678 A | 1/1972 | Seitz et al. ................ 23/230 R |
| 3,650,698 A | 3/1972 | Adler ........................ 23/253 R |
| 3,658,480 A | 4/1972 | Kane et al. ................ 23/230 B |
| 3,692,487 A | 9/1972 | Sanz ......................... 23/253 R |
| 3,695,842 A | 10/1972 | Mintz ........................ 23/230 R |
| 3,699,437 A | 10/1972 | Ur ............................. 324/64 R |
| 3,704,099 A | 11/1972 | Sanz ......................... 23/253 R |
| 3,719,075 A | 3/1973 | Mandrona et al. ............. 73/54 |
| 3,741,002 A | 6/1973 | Simons ........................ 73/64.1 |
| 3,814,585 A | 6/1974 | Bailly ........................ 23/230 B |
| 3,836,333 A | 9/1974 | Mintz ........................... 23/259 |
| 3,911,728 A | 10/1975 | Fixot ............................... 73/55 |
| 3,918,908 A | 11/1975 | Moyer et al. ............... 23/230 B |
| 4,131,549 A | 12/1978 | Ferrara ......................... 210/518 |
| 4,197,735 A | 4/1980 | Munzer et al. ............... 73/61.4 |
| 4,210,623 A | 7/1980 | Breno et al. .................. 422/101 |
| 4,329,302 A | 5/1982 | Hanahan et al. ............. 260/925 |
| 4,443,408 A | 4/1984 | Mintz ............................ 422/73 |
| 4,599,219 A | * 7/1986 | Cooper et al. ................. 422/61 |
| 4,752,449 A | 6/1988 | Jackson et al. ................ 422/73 |
| 4,780,418 A | 10/1988 | Kratzer ........................... 436/69 |
| 4,782,026 A | 11/1988 | Baugh et al. ................... 436/69 |
| 4,788,139 A | 11/1988 | Ryan ............................. 435/13 |
| 4,795,703 A | 1/1989 | Folkman et al. ............... 435/13 |
| 4,871,677 A | 10/1989 | Baugh et al. ................... 436/69 |
| 4,876,069 A | 10/1989 | Jochimsen ...................... 422/73 |
| 5,091,304 A | 2/1992 | La Duca et al. ............... 435/13 |
| 5,174,961 A | 12/1992 | Smith ............................. 422/73 |
| 5,314,826 A | 5/1994 | Baugh ........................... 436/69 |
| 5,705,198 A | * 1/1998 | Triplett et al. ................. 436/69 |
| 5,716,796 A | 2/1998 | Bull et al. ...................... 435/13 |
| 5,925,319 A | 7/1999 | Baugh et al. |
| 5,951,951 A | 9/1999 | Lane et al. |
| 5,972,712 A | 10/1999 | Baugh et al. |

* cited by examiner

*Primary Examiner*—Lyle A. Alexander
(74) *Attorney, Agent, or Firm*—Steven C. Petersen; Sarah J. Smith; Hogan & Hartson, LLP

(57) ABSTRACT

Apparatus and method for evaluating platelet functionality of a blood sample. A cartridge includes a plurality of test cells. Each cell receives an aliquot part of a blood sample. A measured amount of clotting reagent is provided in each cell. A measured amount of platelet activation reagent is provided in each cell, the amount of such reagent in each cell differing from the amount of such reagent in each other cell. The relative clotting times of the aliquot samples in the cells are determinative of the platelet functionality of the blood sample.

21 Claims, 4 Drawing Sheets

TEST CARTRIDGE FOR EVALUATING BLOOD PLATELET FUNCTIONALITY

CROSS-REFERENCE TO OTHER APPLICATIONS

This application is a divisional of U.S. patent application Ser. No. 08/640,275, filed Apr. 30, 1996, now issued as U.S. Pat. No. 5,925,319.

BACKGROUND OF THE INVENTION

1. Field of the Invention

The present invention relates to an apparatus for evaluating blood platelet functionality. More specifically, the invention relates to an improved multicell cartridge for use in evaluating blood platelet functionality and method for using the same.

2. Description of the Prior Art

It has been observed that blood platelets play a significant role in the clotting or coagulation of whole blood. When platelets are activated, they shorten the clotting time of the blood. This shortening is related to the initial status of the platelets and platelet disfunction is considered a leading cause of post-surgical bleeding following cardiopulmonary bypass surgery.

Blood platelet functionality is conventionally determined by mixing blood and a clot promoting reagent such as kaolin in a buffer solution. This is done in a series of test cells incorporated in a test cartridge. After adding the clotting reagent, the blood/kaolin solution in each cell is agitated to activate the platelets to promote clotting. The degree of agitation of the blood sample in each cell differs one from the other. As described in U.S. Pat. No. 5,314,826, the clotting time is proportional to the degree of agitation. By comparing clotting times of aliquots of the blood as a function of degree of agitation, the blood platelet functionality can be determined. This process and the apparatus for carrying it out are disclosed in detail in U.S. Pat. Nos. 4,599,219 and 5,314,826. Where necessary for a further understanding of the present invention, the disclosures in these two patents are incorporated by reference herein.

Chemical platelet activators or reagents are well-known in the art. One such activator, 1-O-alkyl-2-acetyl-sn-glyceryl-3-phosphorylcholine, a biologically active phospholipid, is disclosed in Demopoulos, et al., J. Biol. Chem., 1979; 254:9355–8. This platelet activator or reagent, often referred to as a platelet activating factor, enhances the ability of active platelets to effectively participate in the blood clotting reaction and thereby shorten the clotting time of the blood. If the platelets are inactive or not functioning normally, the activator will have a lessened or no effect on the clotting time.

OBJECTS OF THE INVENTION

It is the principal object of the present invention to provide an improved platelet functionality test cartridge that facilitates the evaluation of functional platelets in a blood sample.

Another object of the present invention is to provide a test cartridge that, upon receipt of blood sample aliquots therein, provides clotting results that are predictive of platelet activity.

SUMMARY OF THE INVENTION

In accordance with the foregoing objects, the present invention is embodied in a cartridge having a plurality of test cells. Each cell is adapted for receiving an aliquot part of a blood sample. A measured amount of platelet activating reagent is applied in the reaction chamber of each cell as a dried fill. The amount of reagent in each cell differs from the amount of reagent in each other cell, at least one of the cells containing no platelet activating reagent. Additionally, amounts of heparin or protamine may be added in each cell either as a liquid or a dried fill. The cells also include a clotting reagent such as kaolin which on use of the cartridge is inserted into the reaction chamber and mixed with the blood and platelet activating reagent. The relative clotting times of the samples in each of the cells are measured and, when compared to a standard and each other, determine the platelet functionality of the blood sample.

The cartridge and method of determining platelet functionality is useful in connection with open heart and cardiopulmonary surgery wherein the blood condition of the patient must be closely monitored.

DESCRIPTION OF THE PREFERRED EMBODIMENT

Figure 4:
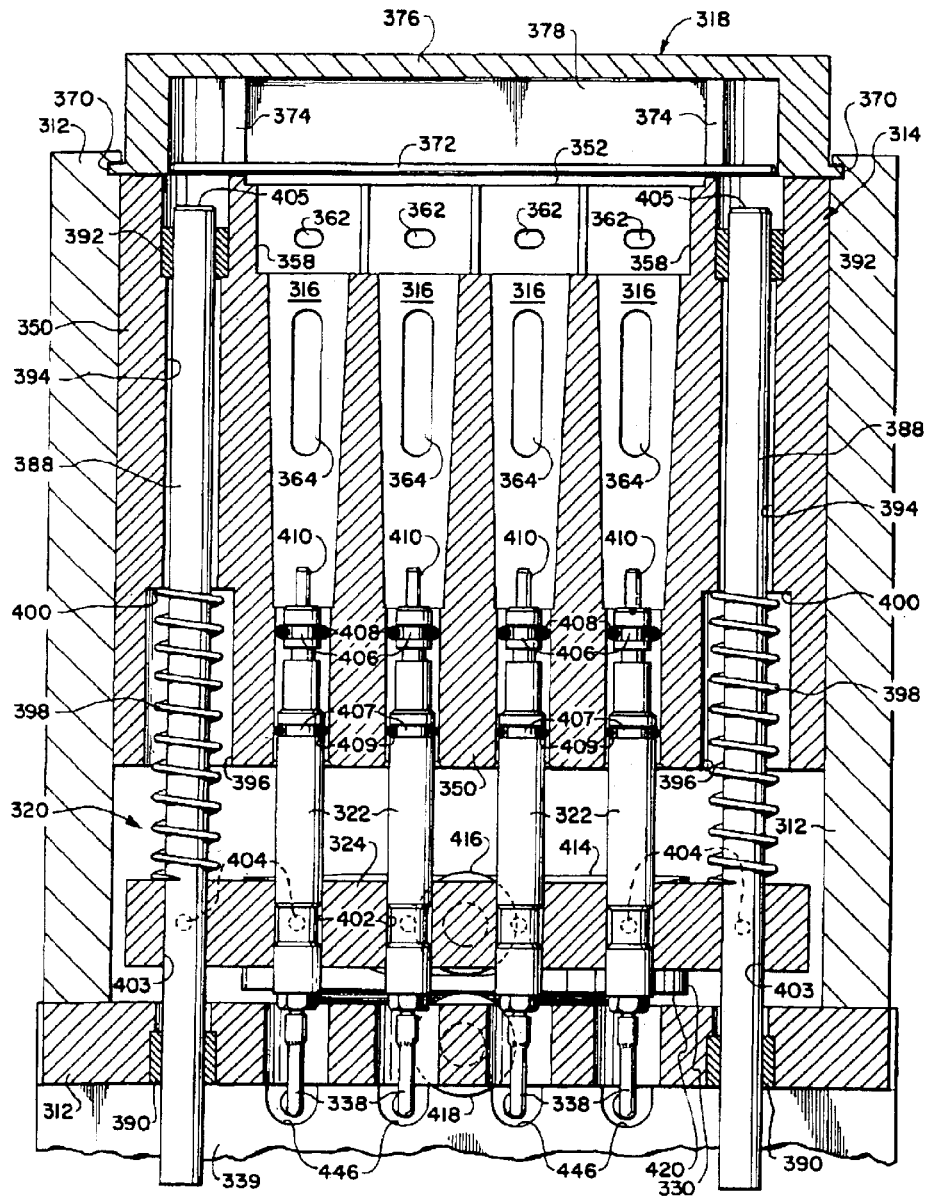
FIG. 4 is a diagram of the closest prior art, showing the actuator mechanism of a plunger sensor cartridge as disclosed on U.S. Pat. No. 4,599,219.

The present invention is embodied in a test cartridge 10 having a plurality of test cells 11, preferably six such cells, depending from and integral with a cartridge plate 12 having a frond depending skirt or panel 14. The cartridge is adapted to be inserted into a test apparatus such as shown in FIG. 4 and described in detail in U.S. Pat. No. 4,599,219 for the determination of clotting time of an aliquot blood sample inserted into each test cell 11 as described in detail in said patent. For example, as described in column 17, lines 24–31 of U.S. Pat. No. 4,599,219, the upward and downward movement of the slide rods 388 also lifts and lowers the lift wire 372. As shown in FIG. 4 of the present invention (FIG. 17 of U.S. Pat. No. 4,599,219), upper ends 405 of the slide rods 388 align with the outer ends of the lift wire 372 when the top cover assembly 318 is in the forward position. As the slide rods move vertically, the ends 405 contact and raise and then lower the lift wire. The plunger assembly 210 is thereby lifted and lowered by the slide assembly. Each cell is formed by a downwardly tapered tube 15 defining an inwardly projecting annular seat 16 intermediate its ends and in turn defining an upper sealing surface 18 and a lower sealing surface 19. A resilient flexible sliding plug 20 is positioned in the lower end of the tube 15 while a plunger 21 defined by a plunger shaft 22 and a sealing washer or disk 24 is positioned in the upper portion of the tube. The sealing washer 24 seats against the upper sealing surface 18 of the annular seat and defines with the plug 20 a lower clotting reagent chamber 25. The tube 15 defines above the washer 24 a blood receiving reaction chamber 26. At its upper end the plunger 21 defines a flag 28 and is adapted for engagement by the test machine (not shown).

A clotting reagent 29, such as kaolin in a buffered, bacteriostatic solution, is contained in the clotting reagent chamber 25 above the plug 20 and below the seal washer 24. When the cartridge is used, the plunger 21 of each cell is lifted and the plug 20 is pushed upwardly, thereby forcing the clotting reagent into the blood sample contained in the upper cell reaction chamber 26 to initiate clotting.

In accordance with the present invention, a measured amount of a chemical platelet activating factor or reagent 30 is provided in the top or upper reaction chamber 26 as a dried fill. This platelet activating factor composition is dissolved in the blood sample when the blood sample is introduced into the upper reaction chamber 26 and the clotting reagent 29 is added and mixed therein. Additionally, selected amounts of heparin or protamine may be utilized as a dried fill in the upper reaction chamber 26, depending on the chemical procedure to be utilized.

Figure 1:
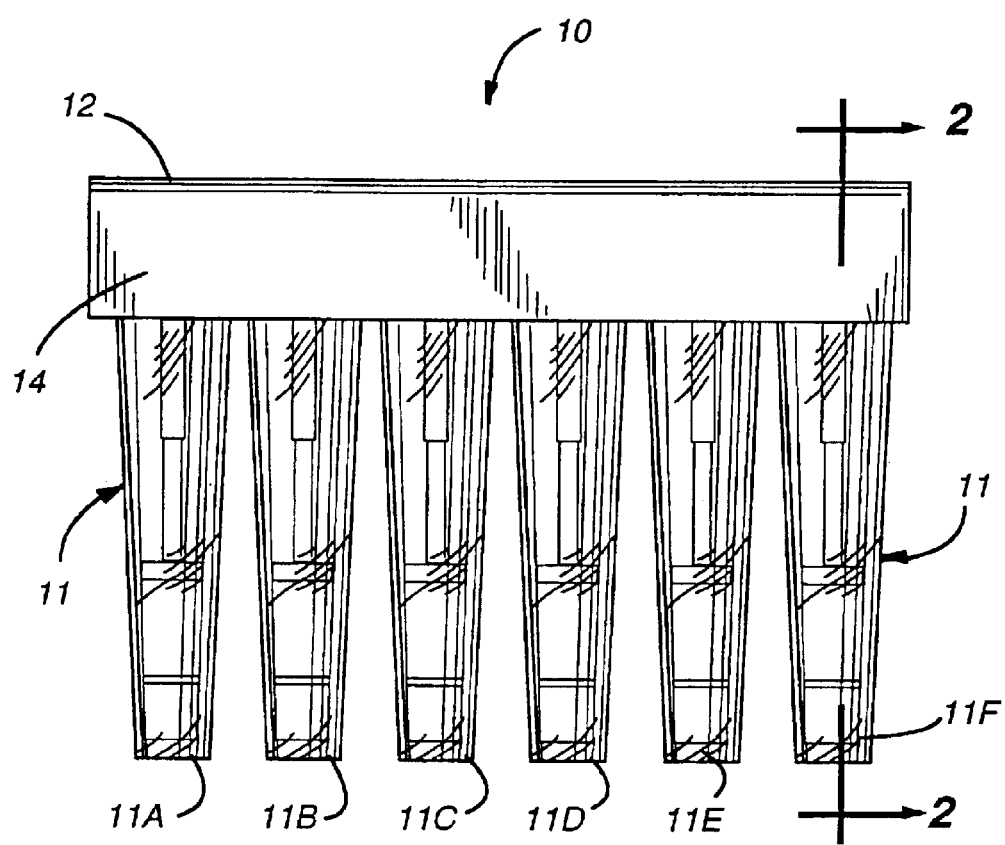
FIG. 1 is a front elevation view of a multicell cartridge embodying the present invention.
Figure 2:
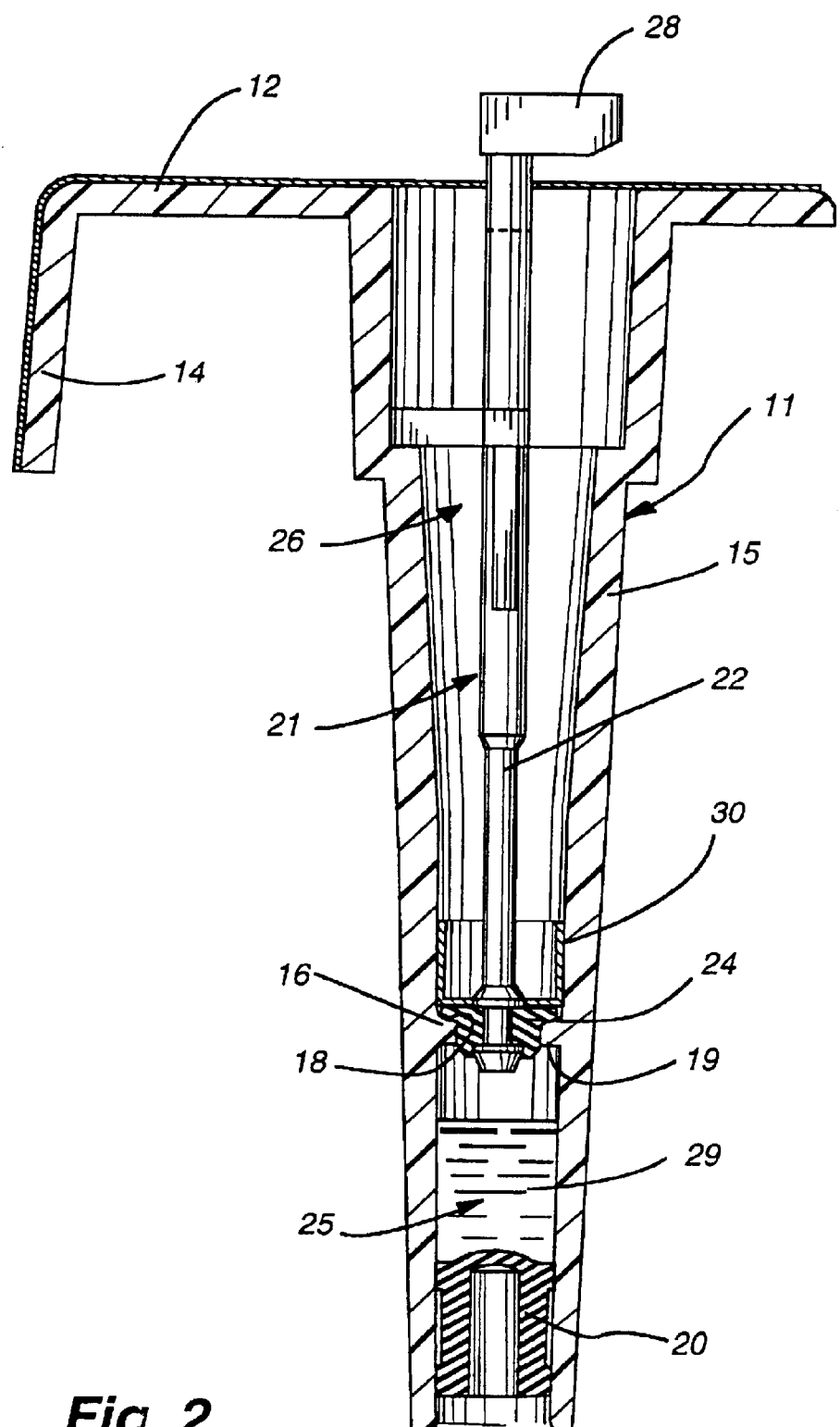
FIG. 2 is a section view taken substantially in the plane of line 2—2 on FIG. 1.

In order to provide a series of differing clotting times, the amount of platelet activating factor in each cell differs from the amount in each other cell. In the first two cells 11A and 11B (as shown in FIG. 1), no platelet activating factor is utilized. In each succeeding cell 11C, 11D, 11E and 11F, increasing amounts of platelet activating factor or reagent are utilized.

The preferred platelet activating factor is the compound 1-O-alkyl-2-acetyl-sn-glyceryl-3-phosphorylcholine, a biologically active phospholipid. Other factors or compounds which may be used are collagen, epinephrine, ristocetin and arachidonic acid. Fills of the preferred platelet activating factor, 1-O-alkyl-2-acetyl-sn-glyceryl-3-phosphorylcholine, are prepared by mixing the factor with a saline (NaCl) solution containing 0.25% bovine serum albumin, and diluting with deionized water to the desired factor concentrations. An amount of each solution of the desired factor concentration is placed in a cell and allowed to evaporate, leaving a solid or dry fill residue of the desired amount of platelet activating factor. Desired amounts of heparin and protamine may also be added and dried as a fill.

The clotting reagent, such as kaolin, is prepared as a 4% w/v suspension in hydroxyethylpiperazine ethanesulfonic acid buffer with 0.5 m calcium chloride, and sodium azide as a bacteriostatic agent. The amount of 0.088 ml of this clotting reagent is loaded into the reagent chamber 25 of each cell 11 of the cartridge 10.

In use, aliquots of 0.35 ml per cell of a blood sample are dispensed into each cell. This results in platelet activating factor (PAF) blood concentrations illustratively shown in the following Table.

TABLE I

Cartridge PAF Concentrations

| Cell A | Cell B | Cell C | Cell D | Cell E | Cell F |
|---|---|---|---|---|---|
| Amount of PAF in Platelet Function-PAF Cartridge | | | | | |
| 0.0 ng | 0.0 ng | 23 ng | 116 ng | 230 ng | 2.76 µg |
| Final Concentration of PAF in Blood | | | | | |
| 0.0 nM | 0.0 nM | 1.25 nM | 6.25 nM | 12.5 nM | 150 nM |

After introducing the blood samples in each upper reaction chamber 26, the clotting reagent is inserted into each upper reaction chamber and the clotting time of the blood in each cell is determined. From the clotting time for each cell, the clot ratio is calculated. Clot ratio is the ratio of the clotting times for cells C, D, E and F compared to the average control clotting times for cells A and B. Platelet function is expressed as a percentage of the maximum clot ratio response observed in a normal population. This value of a normal population response is known and can be used to compute the clot ratio percentage which is in turn indicative of the platelet functionality. Any appropriate desired calculation may be made from the relative clotting times in each cell. The platelet functionality can in turn be utilized to determine blood loss during surgery and the need for a blood transfusion. The platelet functionality further assists in managing heparin therapy during cardiac surgery.

EXAMPLE I

Preparation of Platelet Activating Factor Solutions and Cells

1. Weigh out 62.5 mg Bovine Serum Albumin (BSA) (Sigma Product #A-3803).
2. Weigh out 219 mg NaCl.
3. Make up to 25 ml with deionized water. This gives 0.25% BSA/0.15 M NaCl. Leave until BSA is completely in solution.
4. Using a Hamilton syringe, pipette 50 µl platelet activating factor 1-O-alkyl-2-acetyl-sn-glyceryl-3-phosphorylcholine into a clean stoppered vial and allow to evaporate in a fume hood. Add 2 ml BSA/NaCl solution and leave at least 1 hour. This working stock material is at 100 µM.
5. Dilute the working stock platelet activating factor (PAF) in tenths serially down to 0.1 µM with deionized water. 5 µl of each of these solutions gives 1.25 µM, 12.5 µM, 125 µM and 1250 µM in 0.4 ml blood, respectively.
6. The following amounts are added to the cells and result in the indicated blood concentration:

| Cell | Reagent Added | Concentration of PAF |
|---|---|---|
| A | 5 µl BSA/NaCl | 0 nM |
| B | 5 µl 0.1 µM PAF | 1.25 nM |
| C | 5 µl 1 µM PAF | 12.5 nM |
| D | 5 µl 10 µM PAF | 125 nM |
| E | 2 µl 100 µM PAF | 500 nM |
| F | 5 µl 100 µM PAF | 1250 nM |

Figure 3:
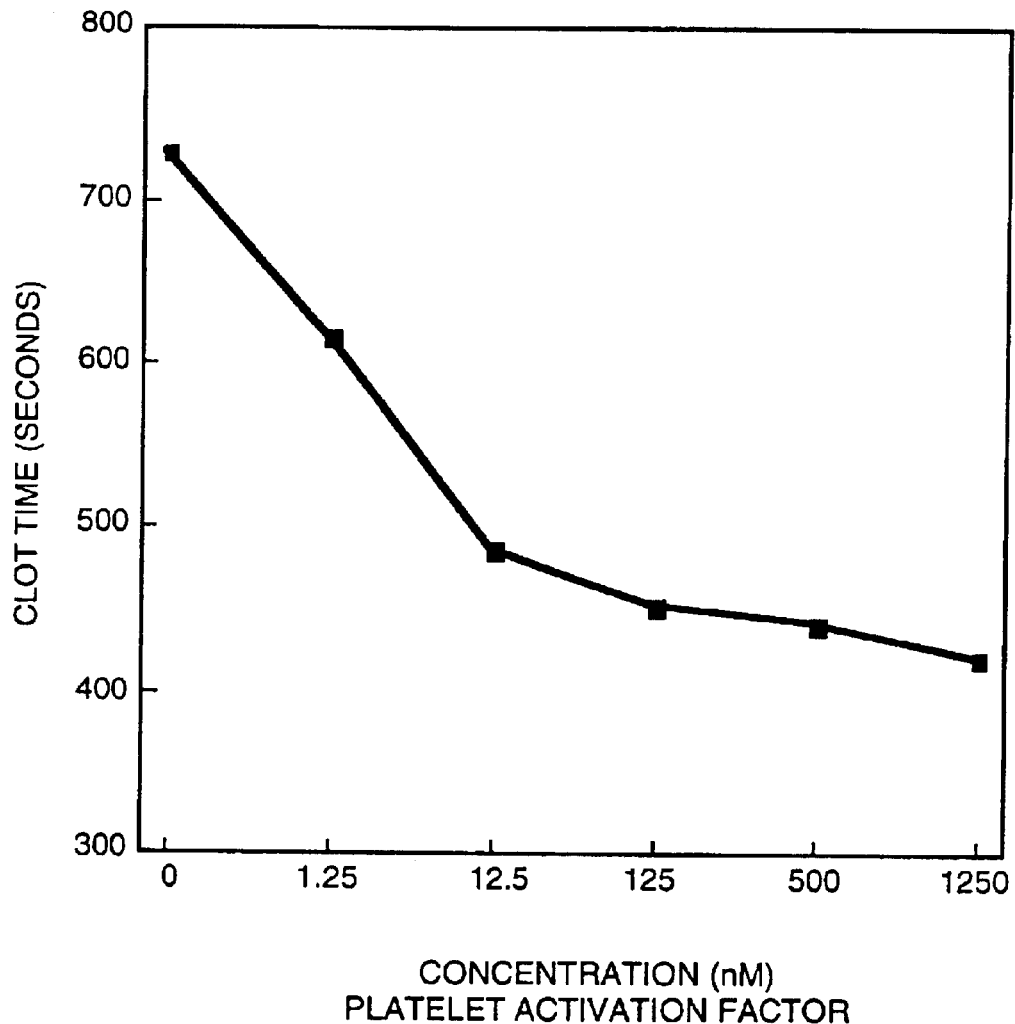
FIG. 3 is a diagram showing the relationship of platelet activating factor concentration to clotting time.

7. The water is allowed to evaporate, leaving a dry fill in each cell.
8. Using a sample of normal blood from a voluntary donor, and a cartridge prepared according to EXAMPLE I, 0.4 ml aliquots of blood were added to each cell and the clotting time of the blood in each cell was determined and plotted as FIG. 3.

As referred to above, the titration curve can be normalized by converting the clotting times to ratios. The clotting time of Cell A, with no platelet activating factor present, is the cell clotting time to which all other cell clotting times are compared. The ratio is calculated by dividing the Cell A clotting time in seconds by each other cell clotting time in seconds. A clot ratio is then calculated as 1 minus the ratio of cell A clotting time to other cell clotting times (1−cellAtime/cellxtime). Data can also be presented in terms of platelet function as a percentage of normal. This is calculated from the clot ratio by multiplying the clot ratio by 100 and then by a factor of 1.97 which has been determined by measuring the maximum platelet activating factor response in 22 normal donors. These donors had no known platelet disfunction and were taking no known medications.

The test cartridge and method described herein are useful for providing a simple and rapid response point-of-care platelet function assay. This assay identifies patients with excessive post-cardiopulmonary bypass blood loss who could benefit from further blood treatment and management.

While a certain illustrative embodiment of the present invention has been shown in the drawings and described above in detail, it should be understood that there is no intention to limit the invention to the specific form disclosed. On the contrary, the intention is to cover all modifications, alternative constructions and compositions, equivalents and uses falling within the spirit and scope of the invention as expressed in the appended claims.

What is claimed is:

1. A method for determining platelet functionality of a blood sample using a plunger sensor apparatus comprising two or more test cells and a plunger assembly within each test cell, the method comprising:

(a) dispensing an aliquot of said sample into each of said test cells;

(b) adding a selected amount of a platelet activating reagent to all but one of said aliquot samples to form a reaction mixture;

(c) adding a sufficient amount of a clotting reagent to each of said reaction mixtures to promote clotting of said aliquot samples;

(d) performing a clotting test on said aliquot samples by alternately lifting the plunger assembly in each cell and allowing the plunger assembly to descend through the test mixture, wherein all of said plunger assemblies are lifted in unison; and (e) determining said platelet functionality of said sample by comparing the clotting times of said aliquot samples, wherein said clotting time of each aliquot sample is determined by measuring a change in viscosity of each of said aliquot samples.

2. The method of claim 1, wherein the amount of said platelet activating agent in each said aliquot sample is between about 0 and about 2.76 micrograms.

3. The method of claim 1, wherein the concentration of said platelet activating reagent in each said aliquot sample is between about 0 and about 150 nM.

4. The method of claim 1, wherein said platelet activating reagent is selected from the group consisting of 1-O-alkyl-2-acetyl-sn-glyceryl-3-phosphorylcholine, collagen, epinephrine, ristocetin and arachidonic acid.

5. The method of claim 4, wherein said platelet activating reagent is 1-O-alkyl-2-acetyl-sn-glyceryl-3-phosphorylcholine.

6. The method of claim 1, wherein said clotting reagent is kaolin.

7. The method of claim 6, wherein said platelet activating agent is 1-O-alkyl-2-acetyl-sn-glyceryl-3-phospohrylcholine.

8. A method for determining clotting characteristics of a blood sample using a plunger sensor apparatus comprising two or more test cells and a plunger assembly within each test cell, said method comprising:

(a) dispensing an aliquot of said sample into each of said test cell;

(b) adding a selected amount of a clotting affecting reagent to all but one of said aliquot samples to form a reaction mixture;

(c) adding a sufficient amount of a clotting reagent to each of said reaction mixtures to promote clotting of said aliquot samples;

(d) performing a clotting test on said aliquot samples by alternately lifting the plunger assembly in each cell and allowing the plunger assembly to descend through the test mixture, wherein all of said plunger assemblies are lifted in unison; and (e) determining the clotting characteristics of said sample by comparing the clotting times of said aliquot samples.

9. The method of claim 8, wherein said clotting affecting reagent is a platelet activating reagent.

10. The method of claim 8, wherein said clotting reagent is kaolin.

11. The method of claim 8, wherein said clotting times are determined by measuring a change in viscosity of each of said aliquot samples.

12. A method for performing an activated clotting time test on a sample of blood using a plunger assembly apparatus comprising a multicell test cartridge, said cartridge comprising at least a first, a second and a third test cell and a plunger assembly within each of said test cells, each of said cells comprising a sufficient amount of a contact activator to achieve clotting, wherein said first cell further comprises a first amount of a platelet activating reagent and wherein said second cell comprises a second amount of said platelet activating reagent, said first and second amounts being different, said method comprising:

(a) dividing said sample into first, second and third partial samples;

(b) dispensing the first partial sample into the first test cell to form a first test mixture;

(c) performing a first activated clotting time test on the first test mixture by reciprocating said plunger assembly within said first cell to obtain a first clotting time;

(d) repeating the aforementioned steps of dispensing and performing an activated clotting time test on each of said second and third partial samples by reciprocating the plungers in said second and third cells at the same rate of reciprocation as in said first cell wherein said plungers in the second and the third cells are lifted in unison to obtain a second and third clotting time; and (e) comparing the clotting time of said first, second, and third partial samples to determine the activated clotting time of the sample of blood based on the clotting time times of said first, second and third partial samples.

13. The method of claim 12, wherein the amount of said platelet activating agent in each said aliquot sample is between about 0 and about 2.76 micrograms.

14. The method of claim 12, wherein at least one of said aliquot samples contains no platelet activating reagent, and wherein each remaining aliquot sample comprises different amounts of said platelet activating reagent.

15. The method of claim 12, wherein said change in viscosity is measured by a plunger sensor technique.

16. The method of claim 12, wherein said platelet activating reagent is 1-O-alkyl-2-acetyl-sn-glyceryl-3-phosphorylcholine.

17. The method of claim 12, wherein said clotting reagent activator is kaolin.

18. The method of claim 12, wherein said platelet activating reagent is selected from the group consisting of 1-O-alkyl-2-acetyl-sn-glyceryl-3-phosphorylcholine, collagen, epinephrine, and ristocetin.

19. The method of claim 12, wherein the concentration of said platelet activating reagent in each said aliquot sample is between about 0 and about 150 nM.

20. The method of claim 12, wherein said clotting times are determined by measuring a change in viscosity of each of said aliquot samples.

21. The method of claim 20, wherein said clotting times are determined by measuring a change in viscosity of each of said aliquot samples.

* * * * *